(12) United States Patent
Gale et al.

(10) Patent No.: US 7,862,830 B2
(45) Date of Patent: Jan. 4, 2011

(54) STEREOCOMPLEX-FORMING COMPOSITION AND IMPLANTABLE MEDICAL DEVICE COMPRISING SAME

(75) Inventors: David C. Gale, San Jose, CA (US); Syed Faiyaz Ahmed Hossainy, Fremont, CA (US); Bin Huang, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 138 days.

(21) Appl. No.: 11/827,912

(22) Filed: Jul. 12, 2007

(65) Prior Publication Data

US 2008/0014240 A1    Jan. 17, 2008

Related U.S. Application Data

(60) Provisional application No. 60/831,020, filed on Jul. 13, 2006.

(51) Int. Cl.
*A61F 2/82* (2006.01)
*A61F 2/06* (2006.01)
*C08G 63/08* (2006.01)

(52) U.S. Cl. .................. 424/422; 525/451; 623/1.15

(58) Field of Classification Search ............... None
See application file for complete search history.

(56) References Cited

U.S. PATENT DOCUMENTS

| | | | |
|---|---|---|---|
| 5,317,064 A | | 5/1994 | Spinu |
| 5,783,504 A | * | 7/1998 | Ehret et al. ............... 442/395 |
| 6,365,173 B1 | | 4/2002 | Bomb et al. |
| 2005/0216074 A1 | | 9/2005 | Sahatjian et al. |
| 2006/0142505 A1 | | 6/2006 | Umemoto et al. |

FOREIGN PATENT DOCUMENTS

WO    WO 02/087411    11/2002
WO    WO 2005/065735    7/2005

OTHER PUBLICATIONS

Yamane et al. Poly(D-lactic acid) as a rheological modifier of poly(L-lactic acid): Shear and biaxial extensional flow behavior. Aug. 2003, pp. 599-609.*
Okihara et al. Crystal Structure of Stereocomplex of Poly(L-lactide) and Poly (D-lactide).*
International Search Report for PCT/US2007/016002, filed 1/16/07, mailed 1/16/08, 6 pgs.
Anderson et al., "Melt preparation and nucleation efficiency of polylactide stereocomplex crystallites", Polymer 47, pp. 2030-2035 (2006).
Schmidt et al., "Polylactide Stereocomplex Crystallites as Nucleating Agents for Isotactic Polylactide", J. of Polymer Science vol. 39, pp. 300-313 (2001).
Slager et al., "Hetero-stereocompexes of D-poly(lactic acid) and the LHRH analogue leuprolide. Application in controlled release", EU J. of Pharmaceutics 58, pp. 461-469 (2004).
Slager et al., "Stereocomplexes based on poly(lactic acid) and insulin: formulation and release studies", Biomaterials 23 pp. 4389-4396 (2002).
Tsuji, "Poly(lactide) Stereocomplexes: Formation, Structure, Properties, Degradation, and Applications", Macromol. Biosci. vol. 5, pp. 569-597 (2005).
Yamane et al., "Poly(D-lactic acid) as a rheological modifier of poly(L-lactic acid): Shear and biaxial extensional flow behavior", J. of Rheology vol. 48, No. 3, pp. 599-609 2004.

* cited by examiner

*Primary Examiner*—Shanon A Foley
*Assistant Examiner*—Sarah Al-Awadi
(74) *Attorney, Agent, or Firm*—Squire, Sanders & Dempsey, L.L.P.

(57) ABSTRACT

The present invention relates to a composition of a first single enantiomer homopolymer and a separate stereocomplex formed of a second single enantiomer homopolymer and it mirror image enantiomer, wherein the first and second single enantiomer homopolymers can be the same or different.

13 Claims, No Drawings

STEREOCOMPLEX-FORMING COMPOSITION AND IMPLANTABLE MEDICAL DEVICE COMPRISING SAME

RELATED APPLICATIONS

This application is derived from and claims the benefit of U.S. Provisional Application Ser. No. 60/831,020 filed Jul. 13, 2006.

FIELD

The current application relates to polymer chemistry, materials science and medical devices in particular to compositions comprising stereocomplexed polymers and implantable medical devices formed therefrom.

SUMMARY

Thus, in one aspect the current invention relates to a composition, comprising from about 50 wt % to about 99 wt % of a first single enantiomer homopolymer; from about 1% to about 50% of a 1:1 blend of second single enantiomer homopolymer, which may be the same as or different from the first single enantiomer homopolymer, with a homopolymer of its mirror-image enantiomer; wherein the blend is prepared using conditions under which a stereocomplex is formed; and the molecular weight of the first single enantiomer homopolymer is sufficiently higher than the molecular weight of each of the homopolymers in the blend such that the first single enantiomer homopolymer forms a continuous phase of the composition and the blend forms a discrete phase of the composition.

In an aspect of this invention, the first and second single enantiomer polymers are the same chemical structure.

In an aspect of this invention the first single enantiomer homopolymer is poly(L-lactide) and its enantiomer for the blend is poly(D-lactide).

In an aspect of this invention the first single enantiomer homopolymer has a molecular weight greater than about 200,000 Da and the each of the homopolymers of the blend has an independent molecular weight that is less than 100,000 Da.

In an aspect of this invention the blend is a 1:1 mixture of the L-enantiomer homopolymer and the D-enantiomer homopolymer.

In an aspect of this invention the blend is a 1:1 mixture of poly(L-lactide) and poly(D-lactide).

In an aspect of this invention the molecular weight of the single enantiomer homopolymer is from about 200,000 to about 500,000 Da.

In an aspect of this invention the molecular weight of each of the homopolymers of the blend is from about 5,000 to about 75,000 Da.

An aspect of this invention is an implantable medical device comprising any of the above-described compositions.

In an aspect of this invention, the above implantable medical device further comprises one or more bioactive agent(s) embedded in the composition.

In an aspect of this invention the above implantable medical device further comprises a coating comprising one or more bioactive agents.

In an aspect of this invention, the above implantable medical device is a stent.

BACKGROUND

Until the mid-1980s, the accepted treatment for atherosclerosis, i.e., narrowing of the coronary artery(ies) was coronary by-pass surgery. While effective and while having evolved to a relatively high degree of safety for such an invasive procedure, by-pass surgery still involves potentially serious complications that, in the best of cases, require an extended recovery period.

With the advent of percutaneous tranluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it other problems such as vasospasm and elastic recoil of the stretched arterial wall which could undo much of what was accomplished and, in addition, it created a new disease, restenosis, the re-clogging of the treated artery due to neointimal hyperplasia.

The next improvement, advanced in the mid-1980s was the use of a stent to maintain the luminal diameter after PTCA. This for all intents and purposes put an end to vasospasm and elastic recoil but did not entirely resolve the issue of restenosis. That is, prior to the introduction of stents, restenosis occurred in from 30-50% of patients undergoing PTCA. Stenting reduced this to about 15-20%, much improved but still more than desirable.

In 2003, drug-eluting stents or DESs were introduced. The drugs initially employed with the DES were cytostatic compounds, compounds that curtailed the proliferation of cells that resulted in restenosis. The occurrence of restenosis was thereby reduced to about 5-7%, a relatively acceptable figure. Today, the DES is the default the industry standard to treatment of atherosclerosis and is rapidly gaining favor for treatment of stenoses of blood vessels other than coronary arteries such as peripheral angioplasty of the femoral artery.

There are several characteristics that are important for implantable medical devices including high radial strength, good fracture toughness, resistance to creep, low stress relaxation, and minimal physical aging. Creep refers to the gradual deformation that occurs in a polymeric construct subjected to an applied load. Creep, for example, can result in an expanded stent retracting radially inward, reducing the effectiveness of a stent in maintaining vascular patency.

There is, therefore, an on-going need for implantable medical devices made of polymers that more completely meet the above criteria. The current invention provides a composition that meets the indicated criteria and implantable medical devices made therefrom.

DETAILED DESCRIPTION

Discussion

Use of the singular herein includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, any words of approximation such as without limitation, "about," "essentially," "substantially" and the like mean that the element so modified need not be exactly what is described but can vary to such an extent that one of ordinary skill in the art would still consider the difference to result in the same as that described. For the purposes of this invention, such variation may be up to ±15% of that set forth in the express description without exceeding the scope of this invention.

A "composition" refers generally to a mixture of two or more ingredients. As used herein, at least one of the ingredients is a polymer comprising a single enantiomer of an optically active monomer, either as a homopolymer or as a discrete block of a block copolymer. Another necessarily present ingredient of a composition of this invention is a stereocomplex formed from a homopolymer of the same single enantiomer above and its corresponding antipodal enantiomer.

An "enantiomer" refers to one of two mirror-image forms of an optically active molecule. The mirror-image forms have exactly the same chemical composition. By optically active is meant that the molecule is capable of rotating the plane of plane-polarized light. The two mirror-image forms rotate plane-polarized light equally but in opposite directions. As used herein, a "single enantiomer" simply refers to one of the two mirror image molecules in an essentially pure state.

As used herein a "blend" refers to an intimate mixture resulting from the thorough mixing of the components of the blend such that the components are individually indistinguishable to the eye.

As used herein, a "continuous phase" refers to an ingredient of a composition that is contiguous throughout the composition, that is, the ingredient forms a single continuous mass.

As used herein, a "discrete phase" refers to an ingredient of a composition herein that is dispersed as isolated masses of the ingredient each mass being completely surrounded by the contiguous continuous phase.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses; vascular grafts, self-expandable stents, balloon-expandable stents, stent-grafts, grafts, artificial heart valves and cerebrospinal fluid shunts. An implantable medical device specifically designed and intended solely for the localized delivery of a therapeutic agent, for example a drug-eluting stent (DES) is within the scope of this invention.

As used herein, a "stent" refers to generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

As used herein, a "bioactive agent" refers to substance that when administered to a patient in need thereof has a beneficial effect on the health and well-being of the patient. This includes, without limitation, curing a disease or disorder with which the patient is inflicted, slowing the progress of a disease or disorder with which the patient is afflicted, eliminating or ameliorating one or more symptoms of a disease or disorder with which the patient is afflicted or preventing or delaying the on-set of a disease or disorder to which the patient is pre-disposed. Examples of bioactive agents include, but are not limited to anti-proliferative, anti-inflammatory, antineoplastic, antiplatelet, anti-coagulant, anti-fibrin, antithrombonic, antimitotic, antibiotic, antiallergic and antioxidant compounds. Thus, the therapeutic agent may be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent such as streptokinase and tissue plasminogen activator, an antigen, a hormone, a growth factor, a ribozyme, a retroviral vector, an anti-proliferative agent such as rapamycin (sirolimus), 40-O-(2-hydroxyethyl) rapamycin (everolimus), 40-O-(3-hydroxypropyl)rapamycin, 40-O-(2-hydroxyethoxy)ethylrapamycin, 40-O-tetrazolylrapamycin, 40-epi(N1-tetrazolyl)rapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins such as sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor such as Angiomax ä, a calcium channel blocker such as nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement such as vitamins, an anti-inflammatory agent such as aspirin, tacrolimus, dexamethasone and clobetasol, a cytostatic substance such as angiopeptin, an angiotensin converting enzyme inhibitor such as captopril, cilazapril or lisinopril, an antiallergic agent such as permirolast potassium, alpha-interferon, bioactive RGD, and genetically engineered epithelial cells. Other therapeutic agents which are currently available or that may be developed in the future for use with implantable medical devices may likewise be used and all are within the scope of this invention.

As used herein, "bioactive agents" includes biobeneficial agents. As used herein, a "biobeneficial" agent refers to a substance beneficially affects an implantable medical device by, for example, reducing the tendency of the device to protein foul, increasing the hemocompatibility of the device, and/or enhancing the non-thrombogenic, non-inflammatory, non-cytotoxic, non-hemolytic, etc. characteristics of the device. Some representative biobeneficial materials include, but are not limited to, polyethers such as poly(ethylene glycol) (PEG) and poly(propylene glycol); copoly(ether-esters) such as poly(ethylene oxide-co-lactic acid); polyalkylene oxides such as poly(ethylene oxide) and poly(propylene oxide); polyphosphazenes, phosphoryl choline, choline, polymers and co-polymers of hydroxyl bearing monomers such as hydroxyethyl methacrylate, hydroxypropyl methacrylate, hydroxypropylmethacrylamide, poly (ethylene glycol) acrylate, 2-methacryloyloxyethylphosphorylcholine (MPC) and n-vinyl pyrrolidone (VP); carboxylic acid bearing monomers such as methacrylic acid, acrylic acid, alkoxymethacrylate, alkoxyacrylate, and 3-trimethylsilylpropyl methacrylate; polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functionalized poly(vinyl pyrrolidone); biomolecules such as fibrin, fibrinogen, cellulose, starch, collagen, dextran, dextrin, hyaluronic acid, heparin, glycosamino glycan, polysaccharides, elastin, chitosan, alginate, silicones, PolyActive™, and combinations thereof. PolyActive™ refers to a block copolymer of poly(ethylene glycol) and poly(butylene terephthalate).

As used herein a "coating" refers to one or more layers of material disposed over the outer surface of an implantable medical device of this invention. By "outer surface" is meant any surface however spatially oriented that is in contact with bodily tissue or fluids. The coating may comprise any of the following individual layers, alone or in any combination: a primer layer, a drug reservoir layer, a rate-controlling layer and/or a topcoat layer.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an intermediary layer between a device body and materials to be affixed to the device body and is, therefore, applied directly to the device body. Examples without limitation, of primers include acrylate and methacrylate polymers with poly(n-butyl methacrylate) being a presently preferred primer. Some additional examples of primers include, but are not limited to, poly(ethylene-co-vinyl alcohol), poly(vinyl acetate-co-vinyl alcohol), poly(methacrylates), poly(acrylates), polyethyleneamine, polyallylamine, chitosan, poly(ethylene-co-vinyl acetate), and parylene-C.

"Disposed over" refers to a relatively thin layer of the material applied, preferably at present, directly to essentially the entire outer surface of the indicated substrate. "Disposed over" may, however, also refer to the application of the thin layer of material to an intervening layer that has been applied to the substrate, wherein the material is applied in such a manner that, were the intervening layer not present, the material would cover substantially the entire outer surface of the substrate.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment.

As used herein a "rate-controlling layer" refers to a separate polymer layer that controls the release of therapeutic agents or drugs from the drug reservoir layer into the environment.

A "top coat layer" refers an outermost layer, that is, a layer that is in contact with the external environment and that is coated over all other layers. The topcoat layer may be a separate layer distinct from drug reservoir layer or the drug reservoir layer may itself be the outermost layer and therefore constitute the topcoat layer of a coating. A separate topcoat layer is often used to provide better hydrophilicity to the device, to better lubricate the device or merely as a physical protectant of the underlying layers.

A "stereocomplex" refers to a specific interaction between two complementary polymeric structures that interlock into a new composite that possesses different physical characteristics from the individual polymers. By "complementary" structures can refer to two polymers that are homopolymers of the individual enantiomers of an optically active molecule such that each polymer is optically active. "Complementary" can also refer to two polymers that bear similar but not identical chemical structures in which case the polymers relate to one another as diasteromers rather than enantiomers. Even further, "complementary" can even refer to unrelated but optically active polymers of opposite polarity that are capable of forming stereocomplexes in which case the stereocomplex is called a "hetero-stereocomplex." For example, without limitation, a heterostereocomplex can be formed between poly(D-lactide) and L-configured polypeptides. All types of stereocomplexes are within the scope of this invention.

While any stereoselective, i.e., optically active, polymer that is capable of forming stereocomplexes may be used in the method of this invention, a presently preferred polymer is polylactic acid. Poly(L-lactide), the homopolymer of one of the mirror-image forms of lactic acid, is a semi-crystalline polymer that exhibits high tensile strength but low elongation to break. It also has a high modulus that affords applications in load-bearing devices such as interference screws, suture anchors, bone anchors and stents. By modulating the degree of crystallinity, the physical properties of the poly(L-lactide) can be manipulated. For instance, increasing the percentage crystallinity increases the tensile strength and modulus and reduces creep and physical aging. "Creep" refers to the permanent deflection of a polymeric object subjected to long-term loading. Such deflection can adversely affect the performance of close-tolerance implantable medical devices such as stents. Physical aging is a phenomenom that results from changes in a polymeric material as it slowly evolves toward thermodynamic equilibrium. That is, when a polymeric material is below its glass transition temperature, Tg, it cannot immediately achieve thermodynamic equilibrium; rather it slowly evolves toward that state. Physical aging is to be differentiated from curing/degradation phenomena (chemical aging, damage, etc.) due to thermoreversibility in that, if a physically aged material is heated above its Tg for a sufficient period of time, the material will behave the same when subsequently quenched below its Tg as following previous quenchings. During the physical aging process, the physical properties of the polymer such as, without limitation, compliance and modulus change continuously. Unless the polymer is at a temperature very close to its Tg, the aging process typically takes months, even years. Since many implantable medical devices are intended to be resident in a patient for corresponding time periods, i.e., months to years, physical aging can have a potentially serious detrimental effect on physical properties of a device made of an aging polymer. As noted above, higher percent crystallinity tends to ameliorate both creep and physical aging.

Too high a crystallinity, however, can result in very low extension to break, that is, a device made of a very highly crystalline material tends to be brittle. Reducing the percent crystallinity helps increase the extension to break, i.e., makes the material less brittle, but at the expense of tensile strength and modulus. The present invention provides a means of achieving both ends, that is, a polymeric composition that exhibits improved tensile strength and modulus, reduced creep and reduced aging while maintaining a favorable extension to break by using a composition that includes a continuous phase homopolymer of a single enantiomer of a stereoselective monomer and a discrete phase comprising a stereocomplex of the same single enantiomer with its mirror image counterpart.

Stereocomplexation of poly(L-lactide) with poly(D-lactide) can favorably improve the physical properties of polylactic acid. Both pure poly(L-lactide) and pure poly(D-lactide) have a melting temperature ("Tm") of approximately 180° C. A blend of poly(L-lactide) and poly(D-lactide), however, has a Tm of approximately 220° C. This increase in Tm is directly attributable to an increase in the stability of the crystalline domain in the blend. Used in implantable medical devices, the increase in stability of the crystalline domain can result in a reduction in physical aging of the polymeric device and a reduction in the amount of creep that the device experiences.

Without being limited by theory, it is believed that the increase in Tm for the blend of poly(L-lactide) and poly(D-lactide) is due to the stereocomplexation of the L- and D-polymers. The stereocomplex is more stable due to the close packing of poly(L-lactide) and poly(D-lactide).

One parameter that may be used to control stereocomplexation is the molecular weight of poly(L-lactide) and poly(D-lactide). In addition, the ratio of poly(L-lactide) and poly(D-lactide) may be varied to control the degree of stereocomplexation. In one embodiment of this invention, poly(L-lactide) is used as the continuous phase in a blend for use in fabricating a stent. The poly(L-lactide) in the continuous phase can have a molecular weight, for example, from about 200,000 to 500,000. In this embodiment, the discrete phase within the poly(L-lactide) continuous phase comprises the blend of lower molecular weight poly(L-lactide) and lower molecular weight poly(D-Lactide). By "lower molecular weight" is meant a molecular weight is less than the molecular weight of the continuous phase. In an embodiment of this invention, the poly(L-lactide) and poly(D-lactide) used to make the stereocomplexed blend of the discrete phase each have a molecular weight less than 100,000 Daltons. The resulting blend has a Tm higher than either poly(L-lactide) or poly(D-lactide).

Other parameters that can affect stereocomplexation include, without limitation, the presence or absence of additives (plasticizers, fillers, stabilizers, etc.) in the composition, the mixing process, applied temperatures, the molding process, any annealing process that might be employed, the solvents used, cooling and heating cycles, pressure and mechanical forces applied and irradiation such as might be applied during sterilization of a implantable medical device. The manipulation and interrelationship among these various parameters are well-known to those of ordinary skill in the art and need not be further explicated herein; the skilled artisan will be able to manipulate the parameters to achieve the disclosures herein.

In an embodiment of this invention, a composition is formed that comprises greater than 50% poly(L-lactide), wherein poly(L-lactide) forms a continuous phase, and less than 50% of a blend of lower molecular weight poly(L-lactide) and lower molecular weight poly(D-Lactide), wherein the blend forms a discrete phase within the continuous phase.

It is understood that the scope of the present invention is not limited to the details of composition and construction set forth above. That is, the invention is capable of other embodiments or of being practiced or carried out in various ways and all such embodiments and ways are within the scope of this invention.

What is claimed is:

1. A composition, comprising:
   from about 50 wt % to about 99 wt % of a first single enantiomer homopolymer, wherein the first single enantiomer homopolymer is poly(L-lactide);
   from about 1% to about 50% of a stereocomplex of a 1:1 blend of a second single enantiomer homopolymer, wherein the enantiomer for the blend is poly(D-lactide), which may have the same or a different chemical composition as the first single enantiomer homopolymer, with a homopolymer of a mirror-image enantiomer of the second single enantiomer homopolymer;
   wherein:
   the molecular weight of the first single enantiomer homopolymer is sufficiently higher than the molecular weight of each of the second single enantiomer homopolymer and its mirror-image enantiomer homopolymer such that the first single enantiomer homopolymer forms a continuous phase of the composition and the stereocomplex blend forms a discrete phase of the composition.

2. The composition of claim 1, wherein the first and second single enantiomer polymers are the same chemical structure.

3. The composition of claim 1, wherein the first single enantiomer homopolymer has a molecular weight greater than about 200,000 Da and the each of the homopolymers of the blend has an independent molecular weight that is less than 100,000 Da.

4. The composition of claim 1, wherein the molecular weight of the first single enantiomer homopolymer is from about 200,000 to about 500,000 Da.

5. The composition of claim 4, wherein the molecular weight of each of the second single enantiomer homopolymer and its mirror image enantiomer homopolymer is about 5,000 to about 75,000 Da.

6. An implantable medical device, comprising the composition of claim 1.

7. An implantable medical device comprising the composition of claim 2.

8. The implantable medical device of claim 6, further comprising one or more bioactive agent(s) embedded in the composition.

9. The implantable medical device of claim 7, further comprising one or more bioactive agents embedded in the composition.

10. The implantable medical device of claim 6, further comprising a coating comprising one or more bioactive agents.

11. The implantable medical device of claim 7, further comprising a coating comprising one or more bioactive agents.

12. The implantable medical device of claim 6, wherein the device is a stent.

13. The implantable medical device of claim 7, wherein the device is a stent.

* * * * *